United States Patent
Pham et al.

[11] Patent Number: 6,103,080
[45] Date of Patent: *Aug. 15, 2000

[54] HYDROCARBON SENSORS AND MATERIALS THEREFOR

[75] Inventors: Ai Quoc Pham, San Jose; Robert S. Glass, Livermore, both of Calif.

[73] Assignee: The Regents of the University of California, Oakland, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/022,168

[22] Filed: Feb. 11, 1998

[51] Int. Cl.$^7$ .................................................. G01N 27/407
[52] U.S. Cl. ...................... 204/424; 204/426; 205/784.5; 205/787
[58] Field of Search ...................... 204/421–429

[56] References Cited

U.S. PATENT DOCUMENTS

| | | | |
|---|---|---|---|
| 4,005,001 | 1/1977 | Pebler | 204/426 |
| 4,024,036 | 5/1977 | Nakumura et al. | 204/427 |
| 4,132,615 | 1/1979 | Linder et al. | 204/428 |
| 4,664,757 | 5/1987 | Zupancic et al. | 204/421 |
| 4,720,335 | 1/1988 | Fukushima et al. | 204/421 |
| 5,387,330 | 2/1995 | Taniguchi et al. | 204/421 |
| 5,453,172 | 9/1995 | Alberti et al. | 204/421 |
| 5,472,580 | 12/1995 | Kennard et al. | 204/421 |
| 5,573,648 | 11/1996 | Shen et al. | 204/421 |
| 5,851,376 | 12/1998 | Nishioka et al. | 204/425 |
| 5,935,398 | 8/1999 | Taniguchi et al. | 204/421 |

Primary Examiner—T. Tung
Attorney, Agent, or Firm—L. E. Carnahan; Alan H. Thompson

[57] ABSTRACT

An electrochemical hydrocarbon sensor and materials for use in sensors. A suitable proton conducting electrolyte and catalytic materials have been found for specific application in the detection and measurement of non-methane hydrocarbons. The sensor comprises a proton conducting electrolyte sandwiched between two electrodes. At least one of the electrodes is covered with a hydrocarbon decomposition catalyst. Two different modes of operation for the hydrocarbon sensors can be used: equilibrium versus non-equilibrium measurements and differential catalytic. The sensor has particular application for on-board monitoring of automobile exhaust gases to evaluate the performance of catalytic converters. In addition, the sensor can be utilized in monitoring any process where hydrocarbons are exhausted, for instance, industrial power plants. The sensor is low cost, rugged, sensitive, simple to fabricate, miniature, and does not suffer cross sensitivities.

21 Claims, 5 Drawing Sheets

HYDROCARBON SENSORS AND MATERIALS THEREFOR

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to sensors, particularly in hydrocarbon sensors, and more particularly to electrochemical hydrocarbon sensors for exhaust monitoring, such as for on-board monitoring and evaluation of the performance of catalytic converters.

Pollution due to the extensive use of internal combustion engines and industry has long been a problem. In the last few decades numerous exhaust purification and emission control systems have been developed. In the automotive arena, preeminent among the current exhaust purification (emission control) systems for internal combustion engines are the catalytic converters.

In recent years, regulations have been instituted which require automobile makers to incorporate comprehensive on-board diagnostic systems into new vehicles. The intent of these regulations is to ensure that the vehicle operator is informed when emission control systems (i.e., the catalytic converter) are no longer performing adequately. Once operators are informed of a malfunction, they will be required to take the vehicle in for repairs so that exhaust emissions are again within the standards set by regulations. Hydrocarbon emissions are currently the main target for control, with an emissions detection limit of 25 parts per million (ppm) in the exhaust stream desired. Currently, there is no hydrocarbon sensor suitable for automobile emissions monitoring, and thus there is a need for a hydrocarbon sensor which has good sensitivity, longevity, and low cost.

The present invention provides a solution for this need by providing a solid-state electrochemical hydrocarbon sensor which offers several advantages for exhaust gas monitoring. Among the properties of the hydrocarbon sensor of this invention are sensitivity, robustness (longevity), and low cost. The invention involves materials and sensor arrangements for a solid-state electrochemical sensor which can be used to monitor hydrocarbon exhaust emissions and which can be used for on-board monitoring of catalytic converters. The sensor of the present invention comprises a proton conducting electrolyte sandwiched between two electrodes, one electrode of which is covered with an appropriate catalyst which catalyzes hydrogen liberation from non-methane hydrocarbons. A protective cover is also used on the assembly and an integrated oxygen pump is employed to remove cross-sensitivities.

SUMMARY OF THE INVENTION

An object of the present invention is to provide a sensor for hydrocarbon exhaust emissions.

A further object of the invention is to provide a sensor for monitoring the amount of hydrocarbons in an exhaust emission.

A further object of the invention is to provide materials for use in sensors for the detection of hydrocarbons.

Another object of the invention is to provide proton conducting electrolytes, and catalyst materials for use in sensors for the detection of hydrocarbons.

Another object of the invention is to provide a protective cover to avoid sensor fouling.

Another object of the invention is to provide an integrated oxygen pump to remove a small cross-sensitivity to oxygen.

Another object of the invention is to provide an electrochemical hydrocarbon sensor for on-board monitoring of vehicle exhaust gas.

Another object of the invention is to provide a hydrocarbon detection approach which is based on the combination of a proton conducting electrolyte and a catalyst that catalyses hydrogen liberation from the hydrocarbons using a variety of catalysts, including dehydrogenation, cracking, and steam reforming catalysts.

Another object of the invention is to provide a hydrocarbon sensor for evaluating the performance of catalytic converters.

Another object of the invention is to provide a hydrocarbon sensor comprising a proton conducting electrolyte sandwiched between two electrodes, wherein at least one electrode is covered with a catalyst.

Another object of the invention is to provide hydrocarbon sensors with different modes of operation; namely, equilibrium versus non-equilibrium measurements and differential catalytic.

Other objects and advantages of the present invention will become apparent from the accompanying drawings and the following description. The present invention comprises a hydrocarbon sensor, basically composed of a proton conducting electrolyte sandwiched between two electrodes. At least one electrode of the assembly is covered with a catalyst. Two different modes of operation for the hydrocarbon sensors can be used: (1) equilibrium versus non-equilibrium measurements and (2) differential catalytic. Various proton conducting materials can be used for the electrolyte and various catalyst materials can be deposited on the electrodes, where desired. The invention, while having application for monitoring hydrocarbon emissions regardless of source, is particularly effective for on-board monitoring of vehicle (auto, truck, train, etc.) exhaust gas and may be effectively utilized for evaluating the performance of catalytic converters and also the emissions from industrial power plants.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

The present invention is directed to hydrocarbon sensors and to materials of various types for use in a solid-state electrochemical sensor which can be utilized, for example, to monitor hydrocarbon exhaust emissions. The sensor is simple in construction and is basically composed of a proton conducting electrolyte sandwiched between two electrodes. A voltmeter is used to measure the voltage developed across the sensor. A Nernstian log-type potential response is observed when the hydrogen ($H_2$) concentration on one side is fixed to serve as a reference and hydrogen concentration on the other side (sample) is varied.

If, on one side of the sensor assembly, a catalytic electrode is used which promotes hydrogen liberation from non-methane hydrocarbons (HCs), the sensor can be used to measure HC concentration. When arriving at the electrode/catalyst surface HCs undergo a decomposition reaction, and hydrogen is liberated which is detected by the sensor.

A large number of chemical reactions can be used for the generation of hydrogen from HCs, including dehydrogenation, cracking, and steam reforming.

When a dehydrogenation catalyst is used, the following reaction (schematic only) occurs:

$$C_nH_m \rightarrow C_nH_{m-2} + H_2$$

When a steam reforming catalyst is used, the following reaction occurs (this reaction involves steam which is also present in the exhaust gas):

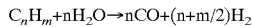

$$C_nH_m + nH_2O \rightarrow nCO + (n+m/2)H_2$$

When a cracking catalyst is used, the following reaction occurs:

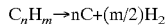

$$C_nH_m \rightarrow nC + (m/2)H_2$$

All of the above reactions produce hydrogen from HCs. Examples of steam reforming catalysts are NiO, nickel metal and precious metals (Pd, Pt, etc.) while $La_{0.9}Ce_{0.1}FeO_3$ is an example of a cracking catalyst.

Figure 1:
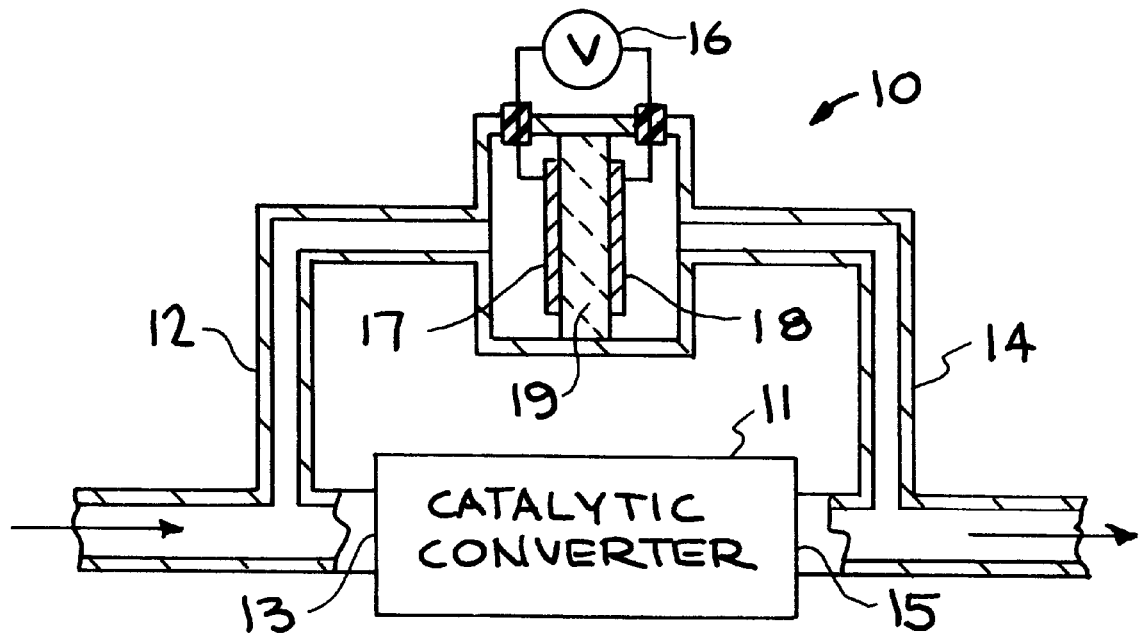
FIG. 1 schematically illustrates an embodiment of a hydrocarbon sensor made in accordance with the present invention, which utilizes the same type of electrodes on both sides of the sensor.
Figure 2:
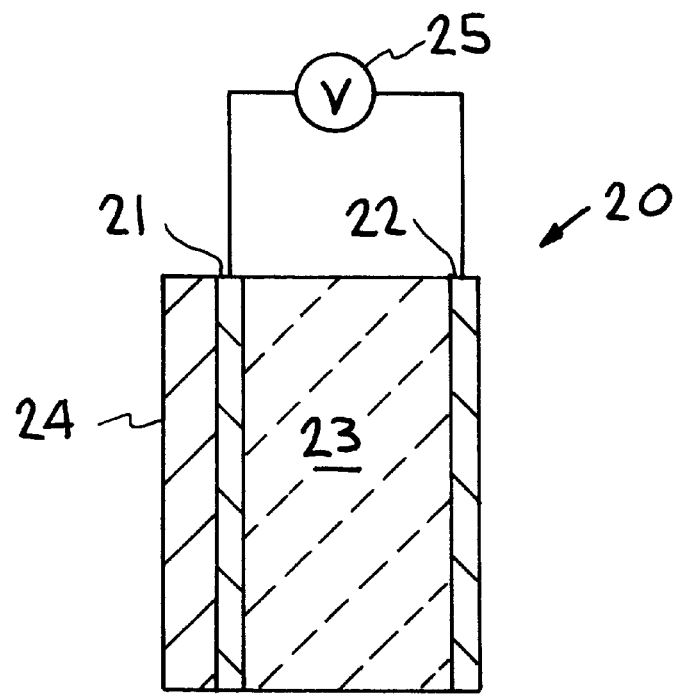
FIG. 2 illustrates an embodiment of the asymmetric hydrocarbon sensor having one electrode located intermediate the electrolyte and a catalyst.
Figure 3:
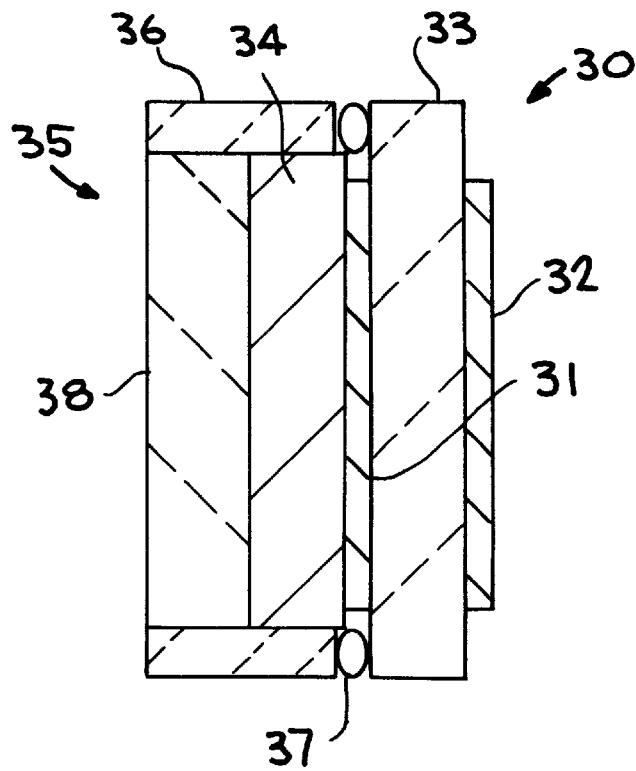
FIG. 3 illustrates another embodiment of the hydrocarbon sensor, similar to that of FIG. 2, wherein one electrode is located intermediate the electrolyte and a catalyst, and a porous protective layer is used.

Two basic types or configurations of the HC sensor are described hereinafter. The first type (Type I) sensor is shown in FIG. 1, and the second type (Type II) sensors are shown in FIGS. 2 and 3. One or both of the electrodes can be covered with a dehydrogenation catalyst depending on the application for the sensor. The Type I sensor (FIG. 1) uses the same electrode materials, with a catalyst coated thereon, on both sides of the proton conducting electrolyte of the sensor. One side (electrode) is exposed to the pre-catalytic converter exhaust gas, the other side (electrode) being exposed to the post-converter exhaust gas. The sensor allows a comparison between the amount of HC in the exhaust gas before and after the catalytic converter, thereby monitoring the HC conversion performance of the catalytic converter. A dead catalyst in the converter would yield a null signal (zero voltage) for the sensor output because the HC concentration would be the same before and after passing through the converter. A functioning catalytic converter, which would produce a much lower HC concentration after the exhaust passes through the converter, would be indicated by a response of up to a few hundred millivolts.

FIG. 1 illustrates an embodiment of a Type I HC sensor and consists of a sensor assembly generally indicated at 10 connected to a catalytic converter 11 via an upstream line 12 adjacent converter exhaust gas inlet 13 and a downstream line 14 adjacent converter exhaust gas outlet 15, with a voltmeter 16 connected across electrodes 17 and 18 between which is a proton conductor or electrolyte 19 of sensor assembly 10. In FIG. 1, electrodes 17 and 18 are coated with a catalyst material. Thus, as exhaust gas indicated by the arrow passes through the catalytic converter 11, the voltmeter attached to electrodes 17 and 18 of sensor 10 indicates the condition of the catalytic material in converter 11. By way of example, the electrodes 17 and 18 may include a coating (a catalytically active material) which extends entirely around the electrodes or only on a surface thereof opposite the electrolyte 19, with the electrodes, the catalyst, and the electrolyte being of any of the exemplary materials described hereinafter with respect to FIG. 2 and FIG. 3.

In the second sensor configuration, the Type II sensor (see FIG. 2), only one electrode is coated with a catalyst. Here, both sides of the sensor are exposed to the same exhaust gas composition exiting the catalytic converter. Decomposition of HCs liberating hydrogen occurs only on the side having the catalyst, thereby generating an $H_2$ concentration difference across the sensor. As a consequence, a voltage develops across the electrodes. This Type II configuration allows a direct measurement of the amount of HCs in the exhaust gas.

The embodiment illustrated in FIG. 2 comprises a sensor cell generally indicated at 20 having a pair of spaced electrodes 21 and 22 between which is a proton conducting electrolyte 23 and with a layer 24 of catalyst in contact with electrode 21. A voltmeter 25 is connected across electrodes 21 and 22. The sensor 20 may be constructed in various configurations (circular, square, etc.).

For the proton conducting electrolyte of FIGS. 1 or 2, for example, the perovskites based on zirconia and ceria, such as $SrZr_{1-x}Ln_xO_{3-\delta}$, $BaCe_{1-x}Ln_xO_{3-\delta}$, and $SrCe_{1-x}Ln_xO_{3-\delta}$, may be used where Ln denotes all the lanthanides plus yttrium and calcium. Y is the preferred dopant (e.g., $SrZr_{1-x}Y_xO_{3-\delta}$) and x ranges from 0 to 0.2, preferably 0.1. Oxygen non-stoichiometry (indicated as $3-\delta$ in $O_{3-\delta}$) is required for proper operation. The zirconia-based materials are preferred because of their greater chemical and mechanical stability. These materials are prepared in powder form using conventional solid-state chemistry techniques. The powder is then pressed into thin (0.5 to 2.0 mm) pellets and sintered at 1500–1600° C.

As to the electrodes of FIGS. 1 and 2, a variety of materials can be used, in particular, the precious metals, such as Pt, Pd, Ag, Au, or their alloys. Metal oxides, commonly used in fuel cell and sensor applications, such as the perovskites $La_{1-x}Sr_xMnO_3$, can also serve as electrodes.

As to the catalysts of FIGS. 1 and 2, compounds such as $Fe_2O_3$ or FeO(OH), which are commercially available, can be used. A new dehydrogenation catalyst of the composition $LaFeO_3$, can also be used. This latter catalyst shows greater stability than the known iron-based catalysts and can be used in the presence of steam. Precious metals (Pt, Pd) supported on porous ceramic materials, such as MgO, $Al_2O_3$, or a silica gel, can also serve as catalysts, although they are not as selective as the iron-based oxides. $La_{1-x}Ce_xFeO_3$ also serves as an effective catalyst to liberate $H_2$ from HCs, although it is not clear whether this is a dehydrogenation catalyst or a cracking catalyst. Finally, nickel oxide can serve as a steam reforming catalyst. The powder catalyst is either mixed with an organic solvent to form a slurry and then painted on top of the sensor electrodes or placed inside a container made of an alumina ring and protected with a porous ceramic layer (see FIG. 3).

The embodiment of the Type II sensor illustrated in FIG. 3 is composed of a sensor cell, generally indicated at 30, which includes a pair of electrodes 31 and 32 separated by a proton conducting electrolyte 33, with electrode 31 being in contact with a layer 34 of a catalyst placed within a container generally indicated at 35, comprising an alumina layer or ring 36, a silver ring 37, and a protective layer 38 of a porous ceramic. While not shown, electrodes 31 and 32 are connected to a voltmeter, as in FIG. 1 and FIG. 2.

By way of example, the electrodes 31 and 32 may be constructed of Pd/Ag alloy paint as a layer having an area of 0.6 cm² and a thickness of a few microns; the electrolyte 33 may be composed of $SrZr_{0.9}Y_{0.1}O_{3-\delta}$ having a thickness of 0.5 to 2.0 mm; the dehydrogenation catalyst 34 may be composed of FeO(OH) having a thickness of 1 to 3 mm, and an area of 0.7 cm²; and the protective layer 38 may be composed of porous $Al_2O_3$ or ZnO, having a thickness of 1 to 5 mm and be of the same thickness and area as catalyst 34. It is to be understood that the sensor 30, in FIG. 3, may be of an annular, square, rectangular, etc., configuration. The silver ring 37 serves as a sealing material to hold the assembly together.

Thin film technology currently exists which can be used to miniaturize the sensor and also enhance sensor sensitivity and lower response time. Thin films of the electrolyte, about 1 micron thick, can be prepared using physical vapor deposition techniques (e.g., dc or rf magnetron sputtering), sol-gel techniques with spin coating, chemical vapor deposition (CVD). The preferred method is tape casting because of its simplicity and low cost, and it is a well-known process. The electrodes are deposited using sputtering or simply by painting the commercially available conductive pastes on the electrolyte. The catalysts are prepared using the citrate technique, also referred to as the Pechini method, in order to obtain a high surface area. Using the known sol-gel technique, the catalyst sol obtained is spin-coated on top of one of the electrodes of the sensor (Type II sensor) or on both sides (Type I sensor).

Figure 4:
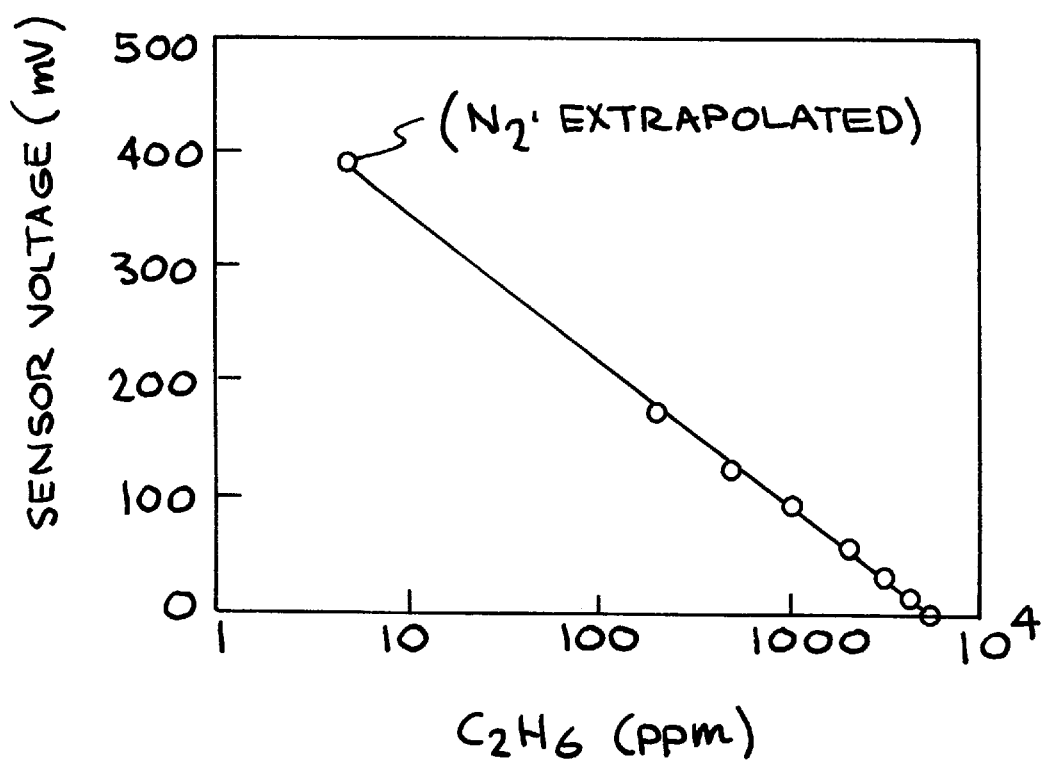
FIG. 4 graphically illustrates typical data from the hydrocarbon sensor of FIG. 2.
Figure 5:
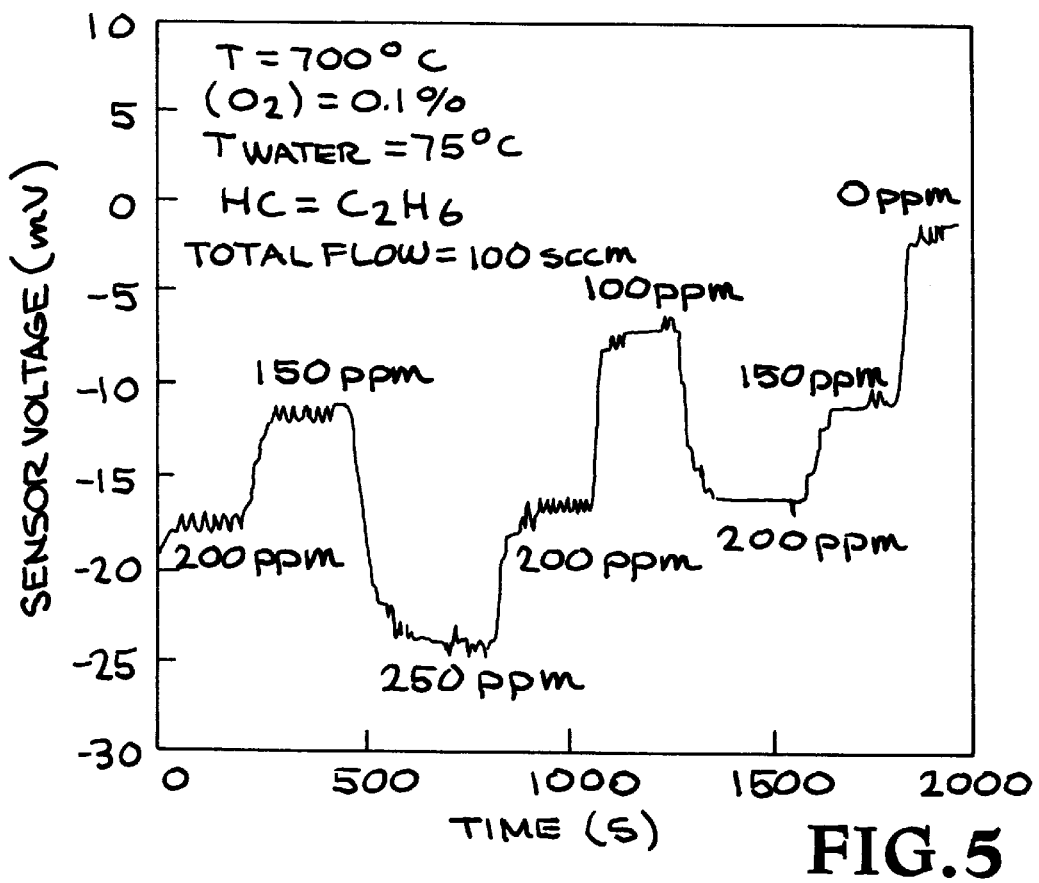
FIG. 5 graphically illustrates the response of the hydrocarbon sensor of FIG. 2 using FeO(OH) as the catalyst.
Figure 6:
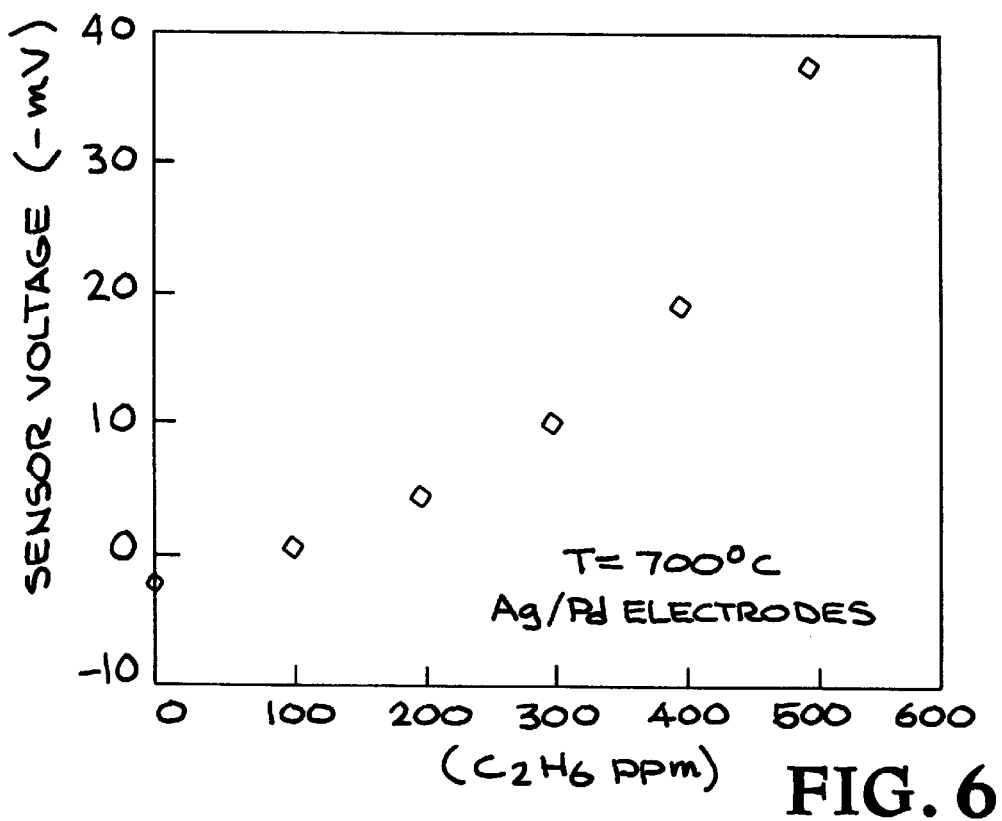
FIG. 6 graphically illustrates the response of the FIG. 2 hydrocarbon sensor using $LaFeO_3$ as the dehydrogenation catalyst and electrodes of Ag/Pd.

FIGS. 4–9 graphically illustrate representative data from the sensor described above. FIG. 4 shows typical data from the Type I sensor (FIG. 1). Here, ethane ($C_2H_6$) was used as the representative hydrocarbon (HC). Ag was used for both electrodes, and $SrZr_{0.9}Y_{0.1}O_{3-\delta}$ was used as the electrolyte. A logarithmic response was observed. FIG. 5 shows the response of a Type II sensor (FIGS. 2 or 3), using FeO(OH) as the dehydrogenation catalyst layer. HC concentrations as low as 50 ppm can be detected. FIG. 6 shows the response of a Type II sensor using the recently developed dehydrogenation catalyst $LaFeO_3$ and using Ag/Pd electrodes.

Figure 7:
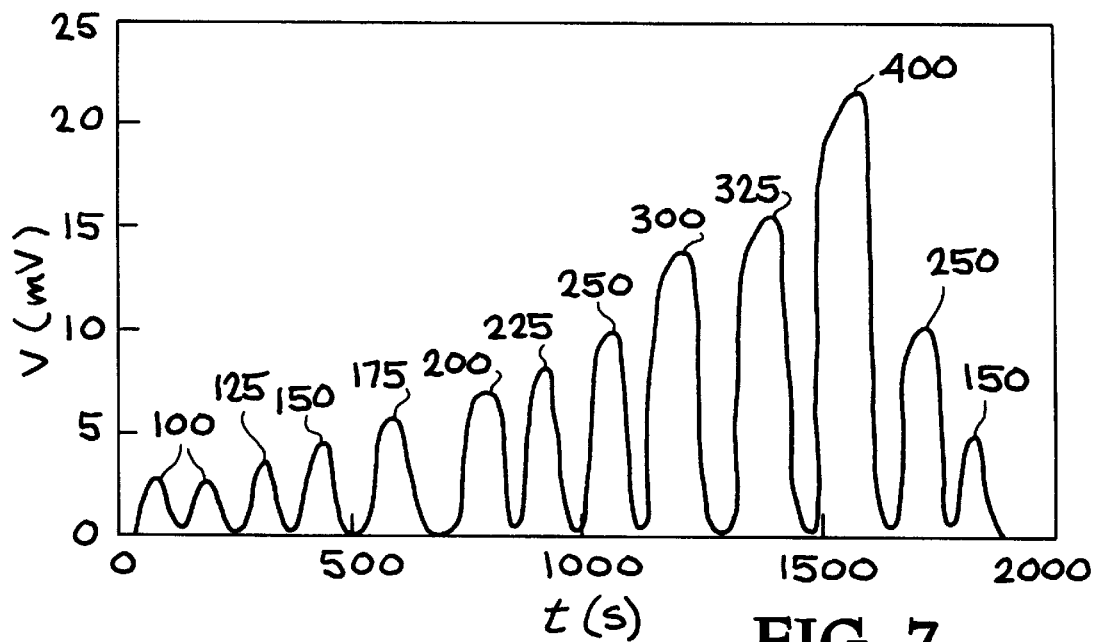
FIG. 7 graphically indicates the response and reproducibility of the sensor of FIG. 2 (using FeO(OH) as catalyst) to varying hydrocarbon concentrations (100 to 400 ppm).
Figure 8:
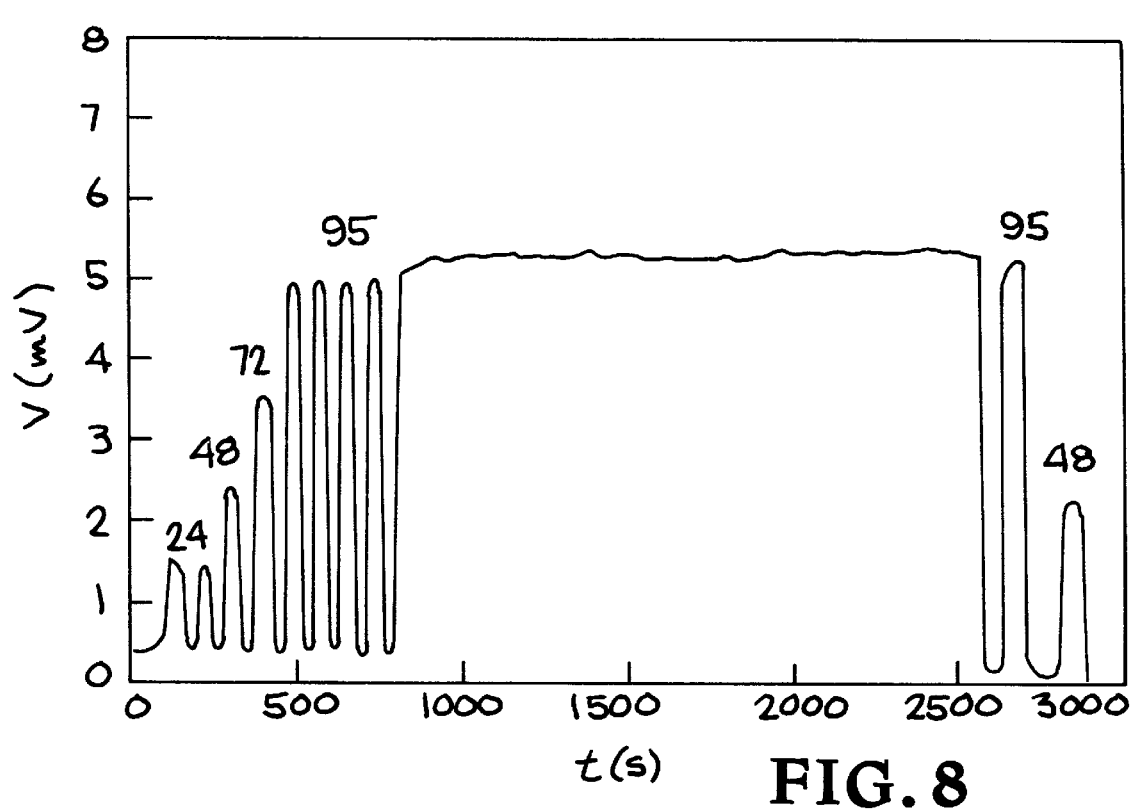
FIG. 8 graphically illustrates the response of the sensor indicated in FIG. 2 (using $LaFeO_3$ as catalyst) to vary the hydrocarbon concentration (using propylene as a model gas) and showing sensitivity below 25 ppm.
Figure 9:
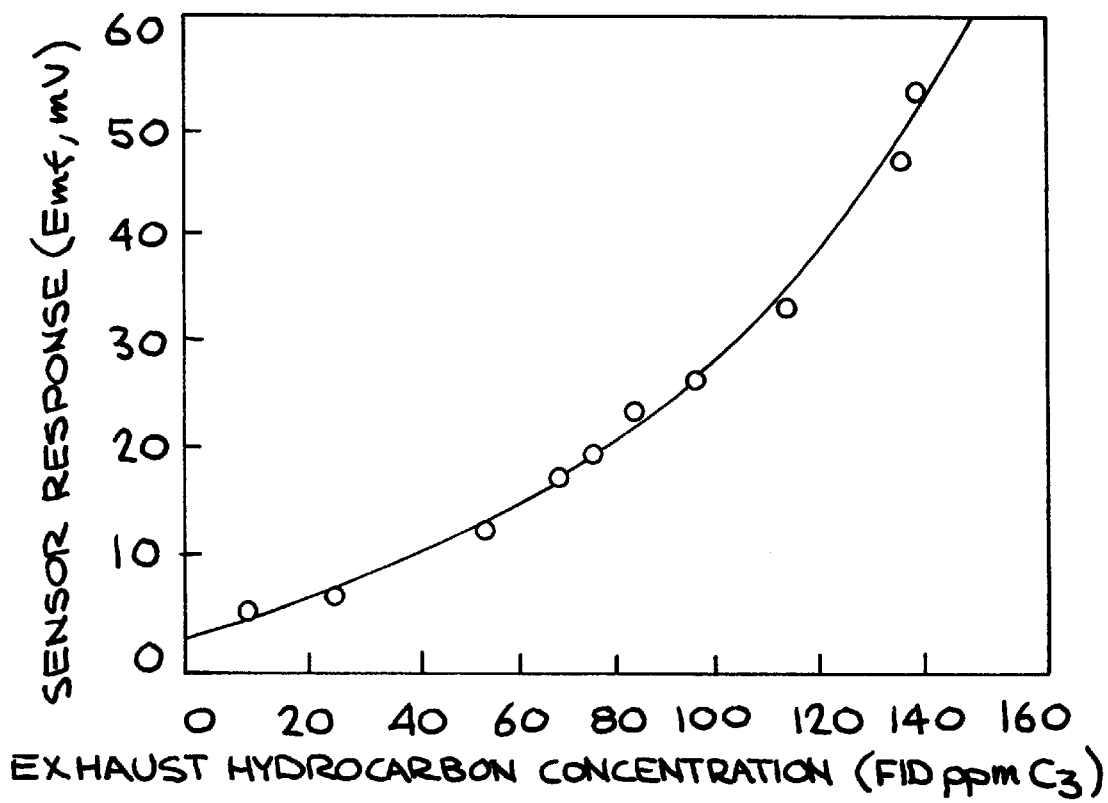
FIG. 9 shows a dynamometer test which compared the sensor response to hydrocarbon concentration (measured downstream) using a standard flame ionization detector.
Figure 10:
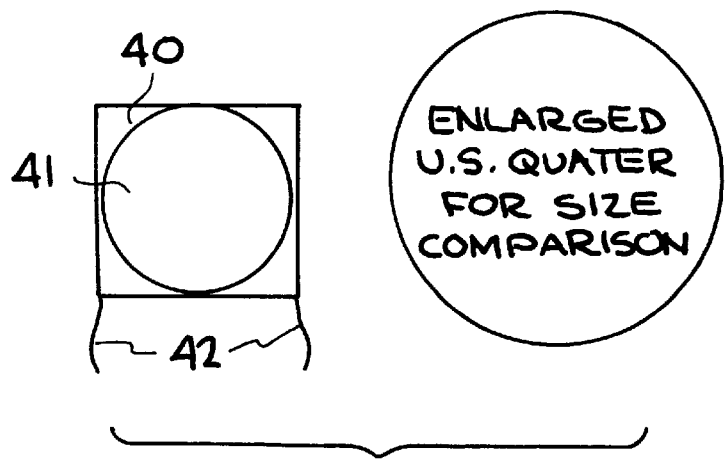
FIG. 10 illustrates the physical size of a test sensor, fabricated in accordance with the thick film processing methods in accordance with the invention, compared to the size of a U.S. quarter.

FIG. 7 further indicates the response and the reproducibility of a Type II sensor [using FeO(OH) as the dehydrogenation catalyst] to varying hydrocarbon concentration (using $C_2H_6$ as a model hydrocarbon) in the range of 100 to 400 ppm. The sensor was operated at 600° C. in a flowing gas stream of 1000 sccm with 0.1 percent $O_2$. In further evidence of the sensitivity of the Type II sensor, FIG. 8 shows data illustrating the sensor response (using the $LaFeO_3$ dehydrogenation catalyst) to propylene as a model hydrocarbon with sensitivity below 25 ppm, which is required for an HC sensor for automotive applications. In FIG. 8, the temperature T was 700° C., with total flow of 1000 sccm and with $O_2$=0.1 percent. Finally, a realistic preliminary evaluation of the sensor has been conducted in actual automobile exhaust. FIG. 9 shows the results of a dynamometer test of the Type II sensor (FeO(OH) as catalyst. A one-to-one correspondence was observed between the sensor response and the HC concentration measured downsteam of the catalytic converter/sensor using the standard flame ionization detector. The physical size of a prototype test sensor is shown in FIG. 10. In this figure, the sensor was fabricated by hand in accordance with the thick film painting/pechini processes described herein and comprises an arrangement similar to that of FIG. 2 and consists of a porous substrate 40, a porous protective cover 41, and wires or leads 42 to a voltmeter, not shown. In addition, it has been determined that the Type II sensor, using $La_{0.9}Ce_{0.1}FeO_3$ as catalyst, exhibits many important advantages, such as very weak (negligible) temperature dependence, high selectivity over other species present in exhaust (namely, CO, $H_2$, and $NO_x$), ruggedness and low cost.

It has thus been shown that the present invention provides a hydrocarbon sensor which can be utilized for hydrocarbon emission monitoring; for example, for on-board monitoring of vehicle exhaust gas, to determine the condition of catalytic converters and for industrial emission monitoring. Various materials may be used in the sensors as the electrodes, proton conducting electrode, and HC decomposition catalysts. The hydrocarbon sensors have two different modes of operation: (1) equilibrium versus non-equilibrium measurements (Type I), and (2) differential catalytic (Type II). Thus the present invention provides for the detection of hydrocarbons wherever such are present in the monitored gas phase and enables measurement of HC exhaust emission concentrations.

While particular embodiments, materials, parameters, etc., have been described and/or illustrated to exemplify and explain the principles of the invention, such are not intended to be limiting. Modifications and changes may become apparent to those skilled in the art, and it is intended that the invention be limited only by the scope of the appended claims.

What is claimed is:

1. A solid-state electrochemical sensor for hydrocarbon exhaust gas emissions, comprising:
   a plurality of spaced electrodes
   at least one said electrodes being provided with a coating containing an HC decomposition catalyst,
   an electrolyte composed of proton conducting doped zirconia material which conducts only protons and which is composed of the perovskites based on zirconia positioned intermediate said electrodes, and
   means operatively connected to said electrodes for detecting a voltage across said electrodes.

2. The sensor of claim 1, wherein said electrodes are constructed of material selected from the group consisting of the precious metals and alloys thereof, and metal oxides.

3. The sensor of claim 1, wherein each of said plurality of electrodes is provided with a catalyst.

4. The sensor claim 1, wherein said catalyst is a steam reforming catalyst.

5. The sensor of claim 1, wherein said catalyst is a cracking catalyst.

6. The sensor of claim 1, wherein said catalyst is a dehydrogenation catalyst selected from the group consisting of $Fe_2O_3$, FeO(OH) and $LaFeO_3$, and precious metals supported on porous ceramics.

7. The sensor of claim 6, wherein said porous ceramics are selected from the group consisting of MgO, $Al_2O_3$ and silica gel.

8. The sensor of claim 1, in combination with a supply of exhaust gas whereby each of said electrodes is in contact with said exhaust gas.

9. The sensor of claim 8, wherein said supply of exhaust gas including a catalytic converter having an inlet and an outlet, and wherein one of said electrodes is connected to receive exhaust gas from said inlet, and one of said electrodes is connected to receive exhaust gas from said outlet.

10. The sensor of claim 1, wherein said catalyst covers only one of said electrodes, and wherein said sensor is positioned directly and uniformly in an exhaust gas downstream from a catalytic converter.

11. The sensor of claim 10, additionally including a container for said catalyst.

12. The sensor of claim 11, wherein said container includes at least one layer of material extending around said catalyst and selected from the group consisting of alumina, MgO and silica; and a protective layer covering a surface of said catalyst and composed of a porous ceramic material.

13. The sensor of claim 12, wherein said container also includes a ring extending around said catalyst and located intermediate said at least one layer and said proton conducting material, said ring being composed of metal.

14. The sensor of claim 1, wherein said electrodes are composed of Ag/Pd, wherein said catalyst is composed of material selected from the group consisting of $LaFeO_3$, FeO(OH), $La_{0.9}Ce_{0.1}FeO_3$, and NiO, and wherein said proton conducting material is an electrolyte composed of $SrZr_{0.9}Y_{0.1}O_{3-\delta}$.

15. A solid state ceramic oxide device for monitoring hydrocarbons in an exhaust gas comprising:

a pair of electrodes, an electrolyte composed of proton conducting doped zirconia material for conducting only protons in contact with each said pair of electrodes, and composed of perovskites based on zirconia, a coating of catalytic material in contact with at least one of said pair of electrodes, and means connected to said pair of electrodes to measure a voltage developed across the device.

16. The device of claim 15, being constructed to operate in two different modes, said two modes being equilibrium versus non-equilibrium, and differential catalytic.

17. The device of claim 15, in combination with a catalytic converter for on-board monitoring of exhaust gas passing through said converter.

18. The device of claim 15, wherein said catalytic material is in contact with each of said pair of electrodes.

19. The device of claim 15, wherein said catalytic material is in contact with only one of said pair of electrodes.

20. The device of claim 15, additionally including means forming a container about exposed surfaces of said catalytic material.

21. A hydrocarbon sensor, comprising:

a pair of electrodes, at least one of said pair of electrodes being provided with a catalyst coating, an electrolyte conducting only protons sandwiched between said pair of electrodes and composed of material which consists of doped zirconia.

* * * * *